(12) United States Patent
Renger et al.

(10) Patent No.: US 9,017,369 B2
(45) Date of Patent: Apr. 28, 2015

(54) TUBULAR MEDICAL INSTRUMENT

(75) Inventors: Uwe Renger, Hilzingen (DE); Martin Blocher, Tuttlingen (DE); Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 1348 days.

(21) Appl. No.: 11/840,486

(22) Filed: Aug. 17, 2007

(65) Prior Publication Data
US 2008/0046003 A1 Feb. 21, 2008

(30) Foreign Application Priority Data

Aug. 17, 2006 (DE) .......................... 10 2006 038 515

(51) Int. Cl.
*A61B 17/00* (2006.01)
*A61B 17/29* (2006.01)
(52) U.S. Cl.
CPC .......... *A61B 17/29* (2013.01); *A61B 2017/0046* (2013.01); *A61B 2017/00477* (2013.01); *A61B 2017/2919* (2013.01); *A61B 2017/292* (2013.01)
(58) Field of Classification Search
USPC .................. 606/108, 127, 205, 206, 208, 210
See application file for complete search history.

(56) References Cited

U.S. PATENT DOCUMENTS

| 5,653,713 A | 8/1997 | Michelson |
| 2006/0259070 A1 * | 11/2006 | Livneh .......................... 606/205 |

FOREIGN PATENT DOCUMENTS

| DE | 14 37 536 | 4/1938 |
| DE | 87 09 151.8 | 11/1987 |
| DE | 43 07 539 | 9/1994 |
| DE | 195 05 032 | 8/1995 |
| DE | 200 20 192 | 3/2001 |
| DE | 102004025041 A1 | 12/2005 |

OTHER PUBLICATIONS

German Search Report, Feb. 9, 2007, 4 pages.
European Search Report; EP 07 01 5245; Jul. 9, 2009; 6 pages.

* cited by examiner

*Primary Examiner* — Victor Nguyen
*Assistant Examiner* — Kevin Everage
(74) *Attorney, Agent, or Firm* — St. Onge Steward Johnston & Reens, LLC

(57) ABSTRACT

The invention relates to a tubular medical instrument having a hollow shaft, a handle positioned on the proximal end of the shaft and equipped with at least two gripping members, and at least one push-pull rod that is positioned in the hollow shaft and has on its distal end a tool consisting of at least two jaw members, wherein for opening and closing at least one jaw member of the tool, the push-pull rod can be coupled with at least one rotatable gripping member of the handle and wherein the push-pull rod and the handle can be detachably connected to one another by a coupling mechanism that is configured as at least one clamping device comprising at least one clamping claw characterized in that the at least one clamping claw can rotate in a guide track mounted between a closed position and an open installation position. To create a coupling mechanism that is easy to handle, it is proposed according to the invention that the at least one clamping claw is mounted in a guide track so that it can rotate between a closed clamping position and an open installation position.

9 Claims, 2 Drawing Sheets

TUBULAR MEDICAL INSTRUMENT

CROSS-REFERENCE TO RELATED APPLICATIONS

The present application claims priority of German patent application No. 10 2006 038 515.2 filed on Aug. 17, 2006, the content of which is incorporated herein by reference.

FIELD OF THE INVENTION

The invention relates to a tubular medical instrument having a hollow shaft, a handle positioned on the proximal end of the shaft and equipped with at least two gripping members, and at least one push-pull rod that is positioned in the hollow shaft and has on its distal end a tool consisting of at least two jaw members, wherein for opening and closing at least one jaw member of the tool, the push-pull rod can be coupled with at least one rotatable gripping member of the handle and wherein the push-pull rod and the handle can be detachably connected to one another by a coupling mechanism that is configured as a clamping device comprising at least one clamping claw.

BACKGROUND OF THE INVENTION

Tubular medical instruments of this type are used, for instance, in the configuration as needle holder, in endoscopic surgery. Because of increasingly stringent hygienic demands, it is more and more often required that tubular instruments, particularly those comprising hollow spaces such as hollow shafts, should be configured so that they can be at least partially dismantled so that they can be submitted to thorough cleansing and sterilization, preferably by steam.

A generic tubular medical instrument, configured as a medical forceps, is reported in DE 43 07 539 A1. This known tubular instrument can be broken down for cleansing and sterilization into three main groups: the push-pull rod, the hollow shaft, and the handle. The coupling mechanism for connecting the push-pull rod with the handle consists, in this construction, of a joint ball that is positioned on the proximal end of the push-pull rod, intended for insertion into a correspondingly formed coupling recess in the rotatable gripping member. This coupling has proved itself in the art, but it requires a very exact manufacturing of the push-pull rod.

Consequently it is the object of the present invention to perfect a tubular medical instrument in such a way that the push-pull rod and the handle can be detachably connected to one another by means of a coupling mechanism that is essentially without play and is easily manufactured.

SUMMARY OF THE INVENTION

This object is fulfilled by the invention in a manner characterized in that the at least one clamping claw mounted in a guide track can be rotated between a closed clamped position and an open installation position.

Because of this configuration of the coupling mechanism as at least one clamping claw mounted in a guide track, an essentially play-free coupling is ensured between the push-pull rod and the handle and also tolerates variations in length of the push-pull rod.

Because of the mounting of the clamping claw in the guide track, the rotation of the at least one clamping claw between the closed clamped position and the open installation position is facilitated, so that through the configuration of the guide for the clamping claw displacement, an exact, uniform motion of the at least one clamping claw into the respective coupling position is ensured. Advantageously, according to the invention, a control peg that engages in the guide track is positioned at each clamping claw mounted in a guide track.

According to a preferred embodiment of the invention, the clamping device comprises two clamping claws.

According to a practical embodiment of the invention, it is proposed that the clamping claws of the clamping device surround the proximal end of the push-pull rod at least partially in form-fitting connection, so that the proximal end of the push-pull rod is configured as a coupling element that can be surrounded at least partially by the clamping claws. The configuration of the clamping claws to grip the proximal end of the push-pull rod allows a space-saving structure for the coupling mechanism along with good force transmission because of the large transmitting surface.

To configure the clamping connection between the clamping claws and the push-pull rod, the coupling element according to the invention is configured as a widening of the push-pull rod mounted downstream in the axial direction of the fixing point formed by the clamping claws. With this configuration it is also possible to secure the push-pull rod in the area of the fixing point either form-fitted or friction-engaged, but in any case clamped by means of the clamping claws.

The coupling element, according to a practical embodiment of the invention, is configured by a constriction of the push-pull rod upstream of the proximal end in the axial direction.

Alternatively, according to a second embodiment of the invention, it is proposed that at least one of the clamping claws should be configured as a spring element, so that the spring elasticity of this at least one clamping claw can be realized not only through the elasticity of the clamping claw material itself, but also through the spring-loading of this at least one clamping claw.

Insertion of the proximal end of the push-pull rod into the clamping device can be facilitated according to the invention in that oblique contact elements are configured on the coupling element and/or on the clamping claws to prevent the tilting of components that run into one another.

It is further proposed with the invention that the clamping claws are positioned so that they can rotate on a connecting member that can be coupled with at least one rotatable gripping member of the handle.

It is finally proposed with the invention that the clamping device is pre-tensed by a spring element into the position that opens the clamping claws in order to allow for simple release of the coupling.

Further characteristics and advantages of the invention can be seen from the appended illustrations, in which an embodiment of an inventive tubular medical instrument is depicted in merely schematic form.

DETAILED DESCRIPTION OF THE INVENTION

Figure 1:
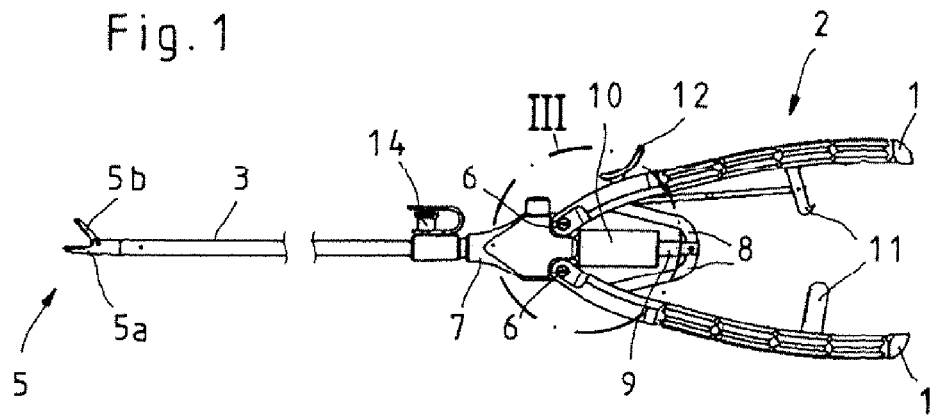
FIG. 1 shows a schematic side view of an inventive tubular medical instrument.
Figure 2:
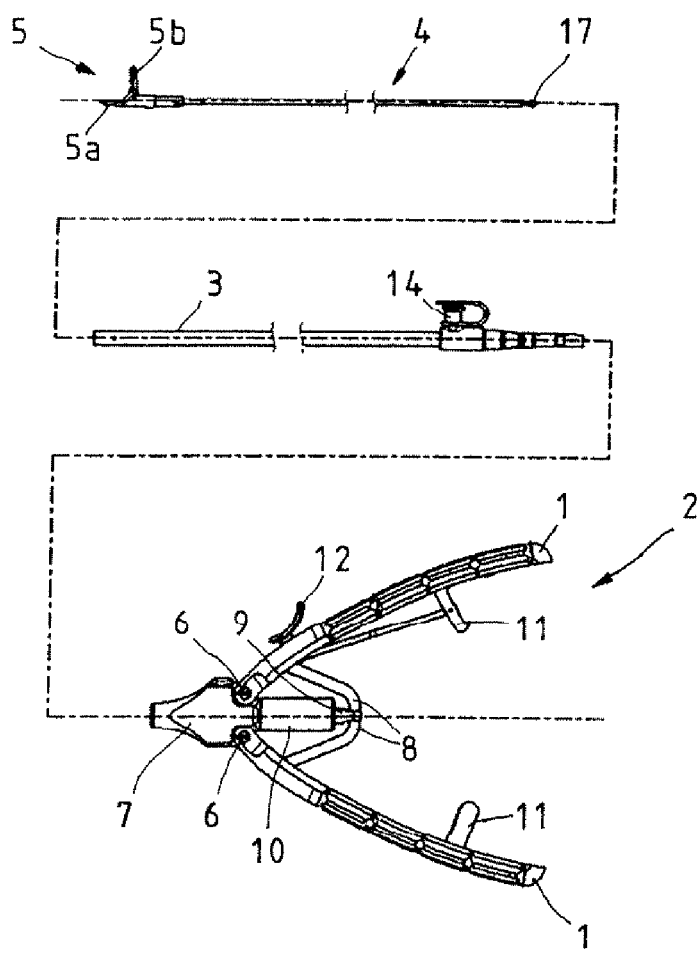
FIG. 2 shows a schematic side view of the instrument of FIG. 1 when dismantled.

The tubular medical instrument seen in FIGS. 1 and 2, configured as a needle holder, consists essentially of a handle 2 equipped with two gripping members 1, a hollow shaft 3, and a push-pull rod 4 that can be inserted into the hollow shaft 3 and has on its distal end a tool 5 consisting of two jaw members 5a and 5b.

The especially clearly depicted components in FIG. 2—the handle 2, hollow shaft 3, and push-pull rod 4—can be coupled with one another by coupling and snap-on mechanisms in such a way that upon actuation of the gripping members 1 of the handle 2 the jaw members 5a and 5b of the tool 5 can be displaced between an open and a closed working position, so that the forces brought to bear by the user on the gripping members 1 of the handle 2 are transmitted by the push-pull rod 4 to the jaw members 5a, 5b of the tool 5.

As in the illustrated embodiment, the tool 5 comprises a rigid jaw member 5a and a jaw member 5b that can rotate with respect to the rigid jaw member 5a. Of course it is also possible to configure both jaw members of the tool 5 as rotatable jaw members 5b.

As can be seen from FIGS. 1 and 2, in the illustrated embodiment both gripping members 1 of the handle 2 are configured as rotatable gripping members 1, which are mounted so that they can rotate by contact points 6 on a housing 7 of the handle 2. To convert the rotary motion of the gripping members 1 into a purely axial motion of the push-pull rod 4 and for force transmission of the pressure force exerted by the user through the handle 2 on the push-pull rod 4, both gripping members 1 are connected by one articulated lever 8 each with a coupling rod 9, which in turn is coupled directly or indirectly by a coupling mechanism with the push-pull rod 4, so that the coupling of the push-pull rod 4 with the coupling rod 9 and thus with the handle 2 occurs in the coupling housing 10.

The coupling of the push-pull rod 4 and thus also of the jaw members 5a and 5b of the tool 5 with the gripping members 1 of the handle 2 is configured so that in pressing together the gripping members 1, the push-pull rod is pulled by the articulated lever 8 and the coupling rod 9 in the axial direction toward the proximal end of the instrument. This axial sliding of the push-pull rod 4 to the proximal end of the instrument causes the jaw members 5a, 5b of the tool 5 to be moved into the closed working position. In this position, pressed together, the gripping members 1 can be fixed with respect to one another by a stopping device 11, so that the user is not required to exert pressure continuously on the gripping members 1 of the handle 2. By means of an unlocking button 12, which separates the parts of the stopping device 11, this fixing can be released again.

Alternatively to the illustrated embodiment, it is also possible of course that the coupling of the push-pull rod 4 and thus also of the jaw members 5a and 5b of the handle 5 with the gripping members 1 of the handle 2 is configured in such a way that the push-pull rod 4 upon pressing together the gripping members 1 is pushed in the axial direction toward the distal end of the instrument.

Figure 3:
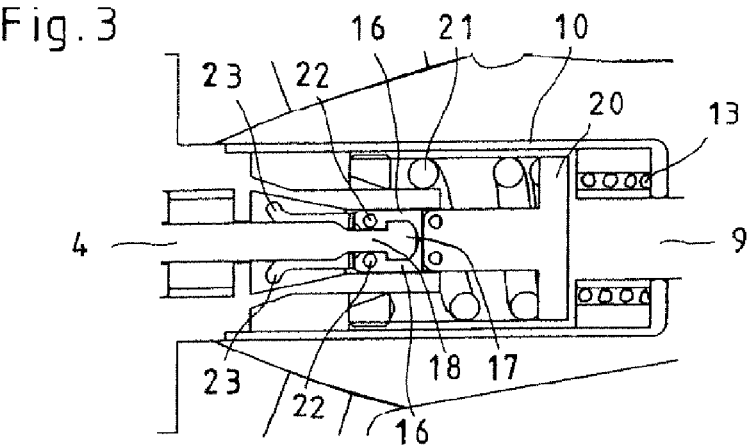
FIG. 3 shows an enlarged partial schematic section of detail III from FIG. 1.

The gripping members 1 are advantageously pre-tensed 13 in the open position by a spring element which, as shown for instance in FIG. 3, is positioned in the coupling housing 10. As soon as the unlocking button 12 is actuated, this spring element 13 pushed the push-pull rod 4 in the axial direction toward the distal end of the instrument, so that the gripping members 1 are pressed apart by the coupling rod 9 and the articulated lever 8. This axial sliding of the push-pull rod 4 toward the distal end of the instrument causes the jaw members 5a, 5b of the tool 5 to be moved into the open working position.

Alternatively to the illustrated embodiment of the handle 2 with two rotatable gripping members 1, it is also possible of course to configure only one gripping member 1 that is rotatable, whereas the other gripping member in that case, for instance, is configured to be in a single unit and rigidly joined with the housing 7 of the handle 2. In such an embodiment it is possible to couple the push-pull rod 4 directly with the rotatable gripping member 1.

The hollow shaft 3 that serves for insertion of the push-pull rod 4 can be coupled with the handle 2 by a coupling or snap-in mechanism that is positioned in the housing 7 of the handle 2. In the illustrated embodiment of the tubular medical instrument, the hollow shaft 3 also comprises a rinsing connection 14, which serves on the one hand to introduce rinsing liquid during an operation and on the other hand can have a rinsing hose connected to it to cleanse the hollow shaft 3.

On the distal side as well, the hollow shaft comprises a coupling or snap-on mechanism, to allow the coupling together of the hollow shaft 3 and the push-pull rod 4 that can be inserted into it.

Figure 4A:
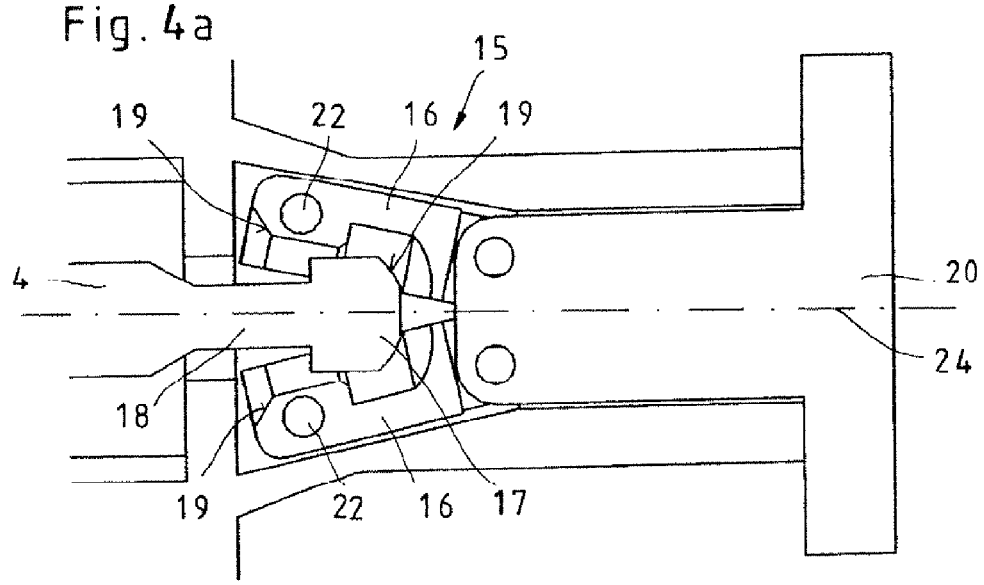
FIG. 4a shows an enlarged partial schematic depiction according to FIG. 3, but presenting the clamping device in the open position.
Figure 4B:
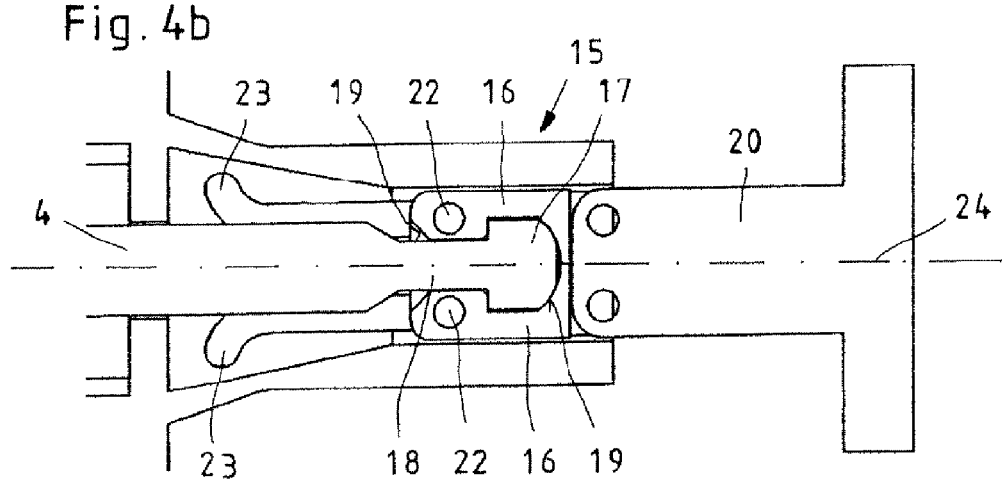
FIG. 4b shows a depiction according to FIG. 4a but presenting the clamping device in the closed position.

The structure of the coupling mechanism that can be positioned in the coupling housing 10 for dissoluble connection of the push-pull rod 4 with the handle 2 can be seen from FIGS. 3 through 4b.

This coupling mechanism is configured as a clamping device 15, which in the illustrated embodiment consists of two rotatably mounted clamping claws 16, which surround the push-pull rod 4 in an at least partial form-fitting connection. For insertion into the clamping claws 16 of the clamping device 15, a coupling element 17 is configured on the proximal end of the push-pull rod 4 and in the illustrated embodiment is configured in hammer-head shape as a constriction 18 mounted upstream of the proximal end in the axial direction.

To facilitate insertion of the coupling element 17 into the clamping claws 16, on the front surfaces of the coupling element 17 and those of the clamping claws 16 that run up against one another, oblique contact elements 19 are configured which serve to reduce the friction resistance of the components that contact one another.

As can be seen from FIGS. 3 through 4b, the two clamping claws 16 are mounted with their proximal ends rotatable on the distal side of a connecting member 20, which contacts the coupling rod 9 by means of a spring element 21, where said coupling rod 9 in turn is coupled with the gripping members 1 by the articulated lever 8. By actuating the gripping members 1 of the handle 2, the clamping claws 16 of the clamping device 15 are thus actuated essentially without any free play, so that coupling of the push-pull rod 4 with the clamping claws 16 can occur exclusively in the installation position shown in FIG. 4a with opened clamping claws 16.

The spring element 21 positioned with the handle 2 in the coupling area of the push-pull rod 4 is a safety device configured as a safety spring 21, which prevents too great a force from being injected into the push-pull rod 4. After the jaw members 5a and 5b of the tool 5 are closed, if the gripping members 1 of the handle 2 are pressed further together, this tractive force that is to be transmitted by the coupling rod 9 and the connecting member 20 onto the push-pull rod 4 is absorbed by the safety spring 21 and thus prevents damage to the push-pull rod 4 and/or to the jaw members 5a and 5b of the tool 5. In securing the clamping connection caused by the clamping claws 16, the safety device likewise prevents possible damage to the connecting member 20 and to the clamping claws 16.

On the distal end the clamping claws 16 are mounted, each by a control peg 22, in a guide track 23. Thanks to this peg-and-groove control, the clamping claws 16 with an axial pushing of the clamping device 15 are moved between the open installation position (FIG. 4*a*) and the closed clamping position (FIG. 4*b*). As can be seen from FIGS. 3 and 4*b*, because the guide tracks 23 run in an outward-bending curve only on their distal ends but otherwise run parallel to the instrument's longitudinal axis 24, the clamping claws 16 can be opened only when the control pegs 22 guiding the clamping claws 16 enter into this curves of the guide tracks 23 on the distal end and thus rotate the clamping claws 16 into the opened installation position.

As an alternative to the illustrated embodiment of the clamping claws 16, it is also possible of course to configured them as spring elements or elastic clamping claws 16, which are pre-tensed by internal stress or an external spring force into the closed position and thus surround the proximal end of the push-pull rod 4 in a form-locking connection.

The composition of the illustrated tubular instrument and in particular of the coupling mechanism for connecting the hollow shaft 3 with the push-pull rod 4 is described hereafter with reference to FIGS. 4*a* and 4*b*.

In the first two installation steps, the push-pull rod 4 and the hollow shaft 3 are coupled to one another and the hollow shaft 3 is connected with the handle 2.

Thereafter the gripping members 1 of the handle 2 are pressed as far apart as possible into the open position, in which they are supported by the spring element 13 positioned in the coupling housing 10. Pressing apart the gripping members 1 of the handle 2 causes an axial motion of the coupling rod 9 by the articulated lever 8 in the direction of the distal end of the tubular instrument.

Through the direct coupling of the coupling rod 9 with the connecting member 20, on which the clamping claws 16 are mounted, the separation of the gripping members 1 of the handle 2 causes further pushing of the clamping claws 16 in the distal direction. Through the peg-and-channel control of the control pegs that engage in the guide tracks 23, the clamping claws 16 in this axial motion are moved into the open installation position illustrated in FIG. 4*a*.

In this position, the push-pull rod 4 can now be inserted into the opened clamping claws 16 with the proximal end, configured as a coupling element 17, forward, a motion that is facilitated by the oblique contact elements 19 configured on both sides. In this open installation position, the gripping members 1 of the handle 2 assume an extra-open position, which said members can never assume in the practical operation of the instrument. This extra-open position of the gripping members 1 serves entirely or the installation of the push-pull rod 4, so that accidental release of the push-pull rod 4 can be excluded in normal operation.

To prevent accidental moving of the gripping members 1 of the handle 2 and thus also of the tool 5 into the extra-open installation position, it is possible, for instance in the area of the proximal end of the push-pull rod 4 and of the hollow shaft 3 mounted in the handle 2, to position a limiting device that restricts the mobility of the push-pull rod 4 within the hollow shaft 3. This limiting device, which is effective only in completely installed tubular instruments, allows an axial motion of the push-pull rod 4 only within the restricted distance that is necessary to rotate the jaw members 5*a*, 5*b* of the tool 5 between the open working position shown in FIG. 1 and the closed working position. Because of the coupling of the axial displacement of the push-pull rod 4 with the angle of rotation of the gripping members 1 of the handle 2, the limiting device that restricts the axial motion of the push-pull rod 4 thus causes at the same time a limitation of the angle of rotation of the gripping members 1 when they are fully installed.

To conclude the installation, the push-pull rod 4 is pressed further in the axial direction all the way to the proximal end of the tubular instrument, a motion that can be supported by pressing together the gripping members 1 of the handle 2. In this axial motion of the push-pull rod 4 in the direction of the proximal end of the tubular instrument, the clamping claws 16 are displaced along the guide tracks 23 proximally, so that said claws move into the closed position that surrounds the proximal end of the push-pull rod 4 in a form-fitting connection. In this position the clamping device 15 causes a coupling of the push-pull rod 4 with the handle 2 that is without free play and reliable.

Dismantling, then, occurs in directly reverse order of the installation steps by releasing the snap-on connection between the hollow shaft 3 and the handle 2, release of the connection of the push-pull rod 4 with the gripping members 1 of the handle 2, and so on to the uncoupling of the hollow shaft 3 from the push-pull rod 4. To release the connection of the push-pull rod 4 with the gripping members 1 of the handle 2, the gripping members 1 are again pressed as far apart as possible until the clamping claws 16 again have assumed the installation position shown in FIG. 4*a* and then the push-pull rod 4 can be uncoupled from the handle 2.

What is claimed is:

1. A tubular medical instrument having:
    a hollow shaft,
    a handle that is positioned on the proximal end of the shaft and equipped with at least two gripping members, and
    at least one push-pull rod that is positioned in the hollow shaft and has a tool on its distal end, the tool consisting essentially of at least two jaw members,
    wherein for opening and closing at least one jaw member of the tool, the push-pull rod can be coupled with at least one rotatable gripping member of the handle,
    wherein the push-pull rod and the handle can be detachably connected to one another by a coupling mechanism that is configured as a clamping device,
    characterized in that the clamping device comprises two clamping claws, each of said clamping claws is positioned in a related separate, guide track which each is configured as a groove in a coupling housing, and each clamping claw being pivotable between a closed position and an open installation position, wherein a control peg is mounted on each clamping claw that is positioned in the related guide track, each control peg being adapted to engage in the related guide track for guiding the clamping claw along the related guide track, and each control peg extending radially outward in a direction transverse to the pivotable movement of the related clamping claw.

2. The tubular medical instrument according to claim 1, characterized in that the clamping claws of the clamping device surround the proximal end of the push-pull rod at least partially in a form-locking connection.

3. The tubular medical instrument according to claim 2, characterized in that the proximal end of the push-pull rod is configured as a coupling element that can be surrounded at least partially by the clamping claws.

4. The tubular medical instrument according to claim 3, characterized in that the coupling element is configured by a constriction of the push-pull rod mounted upstream of the proximal end in the axial direction.

5. The tubular medical instrument according to claim 3, characterized in that at least one of the clamping claws is configured as a spring element.

6. The tubular medical instrument according to claim 3, characterized in that oblique contact elements are configured on the coupling element and/or on the clamping claws.

7. The tubular medical instrument according to claim 2, characterized in that the coupling element is configured as a widening of the push-pull rod mounted upstream of a fixing point formed by the clamping claws in the axial direction.

8. The tubular medical instrument according to claim 1, characterized in that the clamping claws are mounted so that they can rotate on a connecting member that can be coupled with the at least one rotatable gripping member of the handle.

9. The tubular medical instrument according to claim 1, characterized in that the clamping device is pre-tensed by a spring element into the position that opens the clamping claws.

\* \* \* \* \*